(12) United States Patent
Robinson et al.

(10) Patent No.: US 9,700,713 B2
(45) Date of Patent: Jul. 11, 2017

(54) COATINGS FOR ACTIVE IMPLANTABLE MEDICAL DEVICES

(71) Applicant: SALUDA MEDICAL PTY LIMITED, Artarmon, NSW (AU)

(72) Inventors: David Robinson, Artarmon (AU); Mark Fretz, Artarmon (AU); David Thomas, Artarmon (AU); John Luis Parker, Artarmon (AU)

(73) Assignee: SALUDA MEDICAL PTY LIMITED, Artarmon, NSW (AU)

( * ) Notice: Subject to any disclaimer, the term of this patent is extended or adjusted under 35 U.S.C. 154(b) by 448 days.

(21) Appl. No.: 14/360,553

(22) PCT Filed: Nov. 26, 2012

(86) PCT No.: PCT/AU2012/001448
§ 371 (c)(1),
(2) Date: May 23, 2014

(87) PCT Pub. No.: WO2013/075178
PCT Pub. Date: May 30, 2013

(65) Prior Publication Data
US 2014/0324143 A1    Oct. 30, 2014

(30) Foreign Application Priority Data
Nov. 24, 2011  (AU) ................................. 2011904904

(51) Int. Cl.
*A61N 1/05*    (2006.01)

(52) U.S. Cl.
CPC ............. *A61N 1/05* (2013.01); *A61N 1/0551* (2013.01)

(58) Field of Classification Search
CPC ................................ A61N 1/05; A61N 1/0551
See application file for complete search history.

(56) References Cited

U.S. PATENT DOCUMENTS

| | | | |
|---|---|---|---|
| 5,090,422 A | 2/1992 | Dahl et al. | |
| 5,755,762 A | 5/1998 | Bush | |
| 2010/0137928 A1 | 6/2010 | Duncan et al. | |
| 2010/0241204 A1 | 9/2010 | Scheuermann | |
| 2013/0041442 A1* | 2/2013 | Arnholt ................. | A61N 1/056 607/115 |

FOREIGN PATENT DOCUMENTS

WO    WO 02/089909 A1    11/2002

* cited by examiner

*Primary Examiner* — Mark W Bockelman

(57) ABSTRACT

The present invention relates to active implantable medical stimulation devices. An active implantable medical stimulation device comprises an electrically non-conductive support member, one or more electrically conductive stimulation electrodes disposed on the support member and a cover covering the support member and the one or more electrodes. At locations where the cover covers the electrodes, the cover comprises one or more openings dimensioned such that the one or more openings which facilitate electrical conduction to allow stimulation of tissue and/or measurement of electrical signal s by the electrodes while preventing tissue ingrowth. The support member can be of an advantageous structure, that would not be usable without the cover since tissue in-growth would not allow the removal of the implant. At the same time, the cover still allows the stimulation of the tissue so that the functionality of the device is not prevented by the cover.

9 Claims, 5 Drawing Sheets

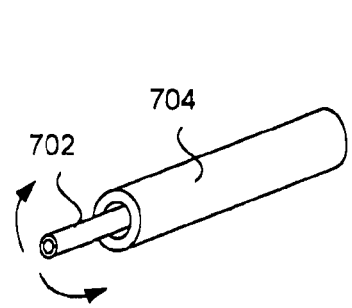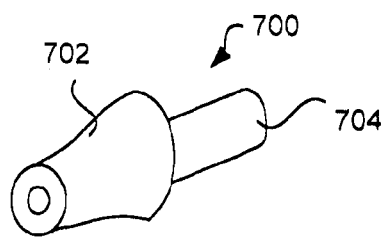
Fig. 7a    Fig. 7b
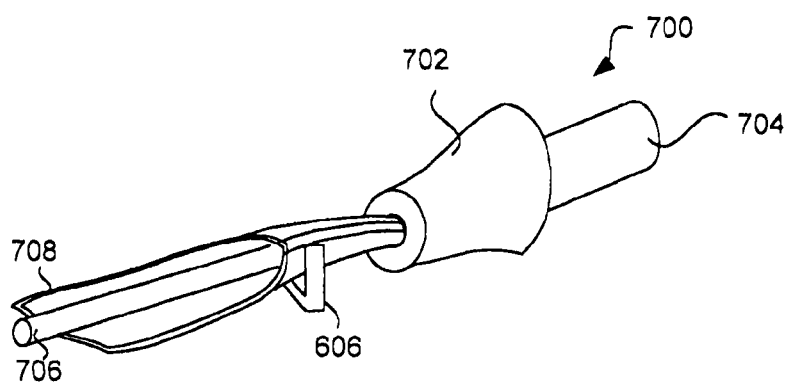
Fig. 7c
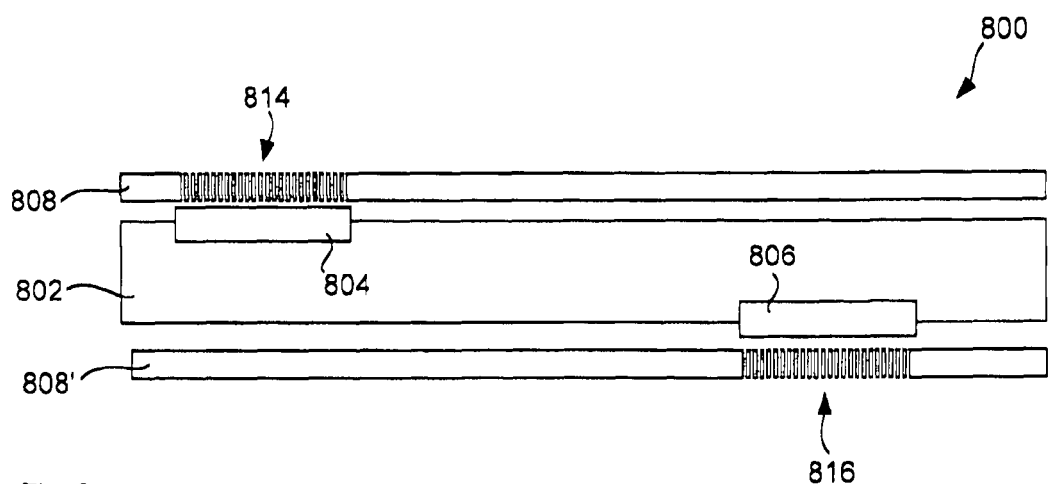
Fig. 8

COATINGS FOR ACTIVE IMPLANTABLE MEDICAL DEVICES

CROSS-REFERENCE TO RELATED APPLICATIONS

The present application claims priority from Australian Provisional Patent Application No 2011904904 filed on 24 Nov. 2011, the content of which is incorporated herein by reference.

TECHNICAL FIELD

The present invention relates to active implantable medical stimulation devices.

BACKGROUND

Medical devices having one or more active implantable components, generally referred to herein as active implantable medical devices (AIMDs), have provided a wide range of therapeutic benefits to patients over recent decades. AIMDs often include an implantable, hermetically sealed electronics module, and a device that interfaces with a patient's tissue, sometimes referred to as a tissue interface. The tissue interface may include, for example, one or more instruments, apparatus, sensors or other functional components that are permanently or temporarily implanted in a patient. The tissue interface is used to, for example, diagnose, monitor, and/or treat a disease or injury, or to modify a patient's anatomy or physiological process.

FIG. 1 illustrates a typical AIMD 100 comprising an electronics module 102 including a power supply, a connector assembly 104, a lead 106 and electrodes 108.

In particular applications, an AIMD tissue interface includes one or more conductive electrical contacts, referred to as electrodes, which deliver electrical stimulation signals to, or receive signals from, a patient's tissue. The electrodes are typically disposed on a biocompatible electrically non-conductive member, and are electrically connected to the electronics module. The electrodes and the non-conductive member are collectively referred to herein as an electrode assembly.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

In a first aspect there is provided an active implantable medical stimulation device, the device comprising:
an electrically non-conductive support member;
one or more electrically conductive stimulation electrodes disposed on the support member; and
a cover covering the support member and the one or more electrodes,
wherein at locations where the cover covers the electrodes, the cover comprises one or more openings dimensioned such that the one or more openings allow stimulation of tissue by the electrodes while preventing tissue ingrowth.

It is an advantage that the dimensioning of the openings allows stimulation while preventing tissue ingrowth. As a result, the support member can be of an advantageous structure, that would not be usable without the cover since tissue ingrowth would not allow the removal of the implant. At the same time, the cover still allows the stimulation of the tissue so that the functionality of the device is not prevented by the cover.

The cover may be a coating.

The cover may be a braid of multiple strands and the openings are formed between the strands.

The strands may be filaments having a diameter, the diameter being such that the strands form openings dimensioned such that the one or more openings allow stimulation of tissue by the electrodes while preventing tissue ingrowth.

The diameter of the filaments may be about 10 micrometer.

The cover may be a porous tape.

The cover may be a porous tube. The tube may be a shrinking tube.

The support member and the one or more electrodes may be formed by a textile technique.

In a second aspect there is provided a method for creating an active implantable medical stimulation device, the device comprising an electrically non-conductive support member and one or more electrically conductive stimulation electrodes disposed on the support member, the method comprising:
forming a cover covering the support member and the one or more electrodes such that at locations where the cover covers the electrodes, the cover comprises one or more openings dimensioned such that the one or more openings allow stimulation of tissue by the electrodes while preventing tissue ingrowth.

The support member may be an open textile structure and forming the cover, comprises filling the open textile structure with a material that prevents tissue ingrowth.

Forming the cover may further comprise:
coating the one or more electrodes with a sacrificial coating before filling the open textile structure; and
removing the sacrificial coating after the filling has cured;
wherein the thickness and size of the sacrificial coating is such that one or more openings are formed in the cover, the openings being dimensioned such that the one or more openings allow stimulation of tissue by the electrodes while preventing tissue ingrowth.

Forming the cover may comprise electrospinning the cover.

Forming the cover may comprise braiding the cover.

Forming the cover may comprise wrapping a porous tape around the support member and the one or more electrodes. The wrapping may be helical.

The wrapping may be coaxial with the support member.

Wrapping the porous tape may further comprise forming an overlap of the tape and bonding the overlap.

The method may further comprise compressing the tape after wrapping the tape around the support member.

Forming the cover may comprise:
locating a tube that has the openings around the support member and the one or more electrodes; and
shrinking the tube Optional features described of any aspect, where appropriate, similarly apply to the other aspects also described here.

BRIEF DESCRIPTION OF DRAWINGS

FIG. 1 is a schematic side view of an AIMD.
An example will now be described with reference to:

FIGS. 7a, 7b and 7c illustrate the creation of a cover using a compression assembly.

FIG. 8 is a cross-sectional view of an active implantable medical stimulation device.

DESCRIPTION OF EMBODIMENTS

Figure 1:
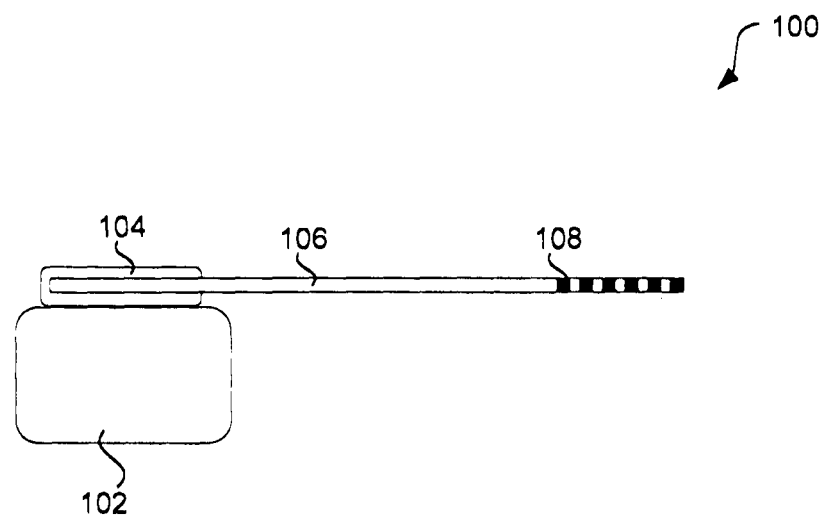

Implantable medical devices such as AIMDs may make use of textile techniques for part or all of their fabrication. Such methods include knitting (warp and weft) braiding and US 2010/0070008 A1 teaches a method of fabricating a catheter-style electrode assembly using textile techniques. While the electrode shown in FIG. 1 is of a style known as a catheter or percutaneous electrode, it will be understood that the subject matter of this disclosure may apply equally to paddle, cuff and all other styles of implantable electrode structures.

Figure 2:
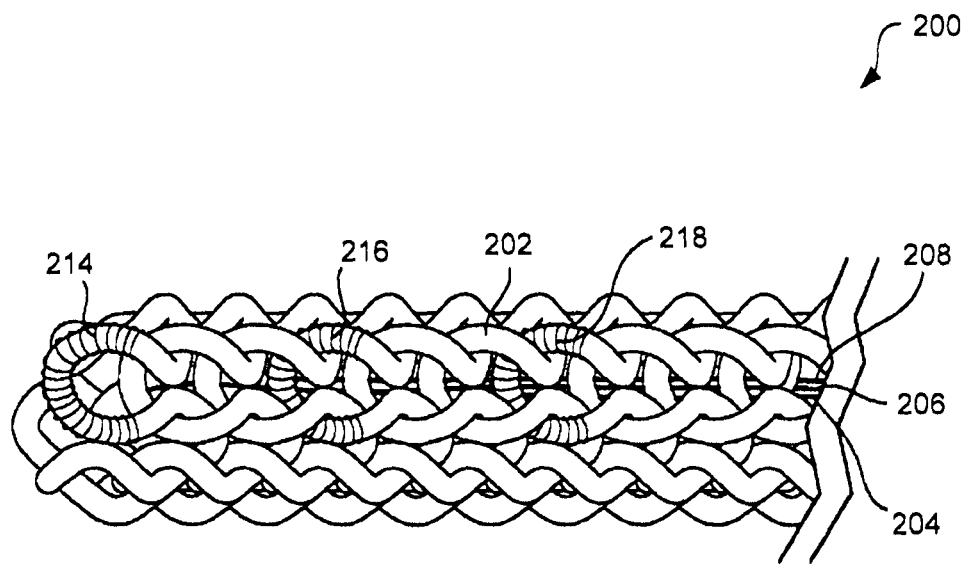
FIG. 2 is a perspective view of a knitted electrode assembly.

FIG. 2 illustrates a knitted electrode assembly 200 comprising a support member that is an open textile structure, such as a knitted, electrically non-conductive support member 202 that constitutes the lead of the AIMD. Open textile structure in this context means that the structure is not tight but has significant amount of space within the structure, such as between the loops of the filament. Therefore, an open structure can be filled with a suitable material to prevent tissue ingrowth as explained below.

The knitted electrode assembly 200 further comprises three conductive filaments 204, 206 and 208, each being connected with one of three electrically conductive stimulation electrodes 214, 216 and 218 which are disposed on the non-conductive support member 202. A more detailed explanation of the knitted electrode assembly can be found in US 2010/0070008 A1. In one example, the stimulation electrodes deliver a charge to the tissue and the charge is determined by a processor integrated into the electronics module 102 in FIG. 1. In another example, only some of the electrodes 214, 216 and 218 are used to deliver a charge to the tissue while the remaining electrodes are used to monitor the electric voltage on the tissue. The measured voltage may then be provided to the processor to update the process of delivering the charge to the tissue. The processor may also select some electrodes for stimulation and some electrodes for measurement such that each electrode provides dual functionality as a stimulation electrode and a measurement electrode.

In the example of FIG. 2, the electrodes 214, 216 and 218 are formed by windings around the nonconductive filament forming the member 202. Other configurations of electrically conductive stimulation electrodes disposed on a non-conductive member are possible, such as a non-knitted member. The design of AIMDs is heavily influenced by the fact that they must be both biocompatible, that is the form of the device and the materials used in the device should not have any deleterious effect on the tissue into which it is implanted, and biosurvivable, that is the device should be able to survive and function properly in the face of biological reactions to its implantation.

There is a sequence/continuum of host reactions following the implantation of a medical device. The general steps of injury, blood material interactions, provisional matrix formation, acute inflammation, chronic inflammation, granulation tissue, foreign body reaction and fibrosis/fibrous capsule development may occur sequentially or may overlap or occur simultaneously.

The encapsulation of foreign bodies with fibrous tissue may be desirable in some implantable textile applications such as tissue scaffolds where the propensity of the textiles to accept fibrous tissue in-growth is key to the intended function of the textile device. In the case of catheter style electrodes, however, this is not an advantage. For such leads which include a tissue interface, such as electrodes, it is advantageous that the implanted structure can be removed should the lead fail or its positioning need to be revised. Such a stimulation device allows for the possibility of explanting, that is, reversing the implantation, and so it is an advantage that the stimulation device prevents tissue in-growth to the fabric structure.

Some forms of the textile catheter style of lead described in US 2010/0070008 A1 may be susceptible to fibrous tissue in-growth. Some textile forms, such as knitting, may create relatively large pore sizes which may allow the vascularisation of fibrous tissue.

Some leads solve this problem by choosing a smooth construction. This design choice may introduce other design limitations which effect tensile strength, fatigue life and electrode size.

In other cases the tissue interface of an AIMD (which may or may not be of a textile construction) may be enhanced by micro-structuring the surface of the electrode. U.S. Pat. No. 5,326,448 teaches of one such a method. This is one of a class of surface treatments that can be used to micro-structure the surface of an electrode and thereby increase the surface area and decrease the electrode impedance. However, tissue ingrowth into the micro-structure isolates the electrodes and therefore, reduces the effectiveness of the stimulation electrodes. Further, since the micro-structure is very delicate, a small force is sufficient to permanently damage the electrode. Any ingrown tissue acts as a mechanical connection between the electrode and the surrounding tissue. During natural movement of the AIMD relative to the tissue, the tissue that is grown into the micro-structure exerts a force onto the micro-structure that damages the micro-structure such that the electrodes become ineffective.

It is therefore desirable to provide a cover over such micro-textured surfaces to prevent tissue ingrowth while still providing a conduction path to the micro-textured electrode. Such a cover also provides protection from mechanical damage to the micro-textured surface.

An active implantable medical stimulation device that substantially ameliorates the problem of tissue ingrowth and/or mechanical damage comprises a non-conductive member 202 and electrically conductive stimulation electrodes 214, 216 and 218 and a cover covering the member 202 and the electrodes 214, 216 and 218. At locations where the cover covers the conductive stimulation electrodes 214, 216 and 218, the cover comprises one or more openings dimensioned such that the one or more openings allow stimulation of tissue while preventing tissue ingrowth.

The cover is bio-compatible and sufficiently porous to allow for the passage of ions through pores in the covering, but which has pore sizes sufficiently small to ensure no tissue ingrowth (to facilitate explant or revision). The immediate (minutes to hours) reaction of the body to the injury of vascularised tissue is the development of the provisional matrix at the implant site. This provisional matrix appears to provide both structural and biochemical elements required for wound healing. Ultimately the creation of sustainable tissue in any part of the provisional matrix depends on the body's capacity to vascularise that tissue. As early as a few days after the implantation of an AIMD, biomaterial granulation tissue will start to form. In this stage new small blood vessels start to appear. Since any viable capillary must be large enough to carry red blood cells (approximately 5 μm across) and vascularisation must provide for the supply and return of blood to tissue, pores in a biomaterial of approximately 10 μm or less are too small to allow for the development of long-term vascularisation or tissue development. It is also desirable that any cover over an electrode structure impede the transport of ions as little as possible. Pores with a size between 0.5 microns and 10 microns are generally suitable. In the preferred embodiment pore sizes are between 2 and 5 microns.

Several methods of achieving the desired cover, such as a coating, are: coating the lead with a porous polymer, covering the lead with a porous membrane (e.g. a non-woven material) with a suitable pore-size and covering the lead with a woven textile structure (e.g. a suitable braid). These methods will be described in further detail below.

One example is to fill the open textile structure with a flexible biocompatible material that will prevent tissue ingrowth. Such materials should effectively fill any pores in the structure while not causing the lead to become too stiff. Low durometer silicones may be such a suitable material. However it will be noted that the electrodes in the leads described in US 2010/0070008 A1 are formed on or coincident with the yarn or yarns that form the lead. If the material used to fill the textile structure is non-conductive in nature and it covers the electrode structures then they will be electrically isolated from the tissue or electrolyte and stimulation will be impossible.

Two methods are described to effect this approach. The first method is to use an electrically conductive filling material. Such materials may be inherently conductive, for example, a conductive hydro-gel. In another example, the coating may be effected by covering the underlying structure with a biocompatible polymer coating, such as biospan, or by filling the underlying porosity with a biocompatible polymer, such as silicone.

The polymer material may be inherently conductive, such as described in "Self-assembled monolayers of polythiophene conductive polymers improve biocompatibility and electrical impedance of neural electrodes"—Alik S. Widge, Malika Jeffries-El, Xinyan Cui, Carl F. Lagenaur, Yoky Matsuoka—Biosensors and Bioelectronics 22 (2007) 1723-1732.

In yet another example, the polymer material is porous to electrolyte, which means that the polymer material has openings at least where the cover covers the electrically conductive stimulation electrodes.

In one example, the porosity is achieved by mechanical means, such as laser drilling suitable size openings through the material over the conductive portion. Another example, where the non-conductive material is silicone, is to add finely ground biocompatible material that is soluble in a biocompatible fluid (e.g. NaCl or sucrose) to the silicone before it cures. Once the material has cured the NaCl can be dissolved out of the structure. Provided the resulting pores are of an appropriate size this approach results in openings that provide a conduction path for ions while resisting fibrous tissue ingrowth.

Another example involves coating the conductive parts of the electrode structure with a biocompatible sacrificial coating (such as polyethylene glycol or PEG). In this approach the conductive elements are coated with such suitable material and then the textile lead structure is coated with a suitable non-conductive polymer. Once the polymer has cured the sacrificial coating is removed (e.g. by dissolving in a suitable solvent). Once the sacrificial coating has been removed the resulting openings will allow electrolyte to penetrate the lead and create a conduction path. It will be understood that the thickness of the sacrificial coating is such that the resulting opening is dimensioned to resist tissue ingrowth.

Another exemplary approach to prevent tissue ingrowth into an open structure textile lead is to create the cover as an outer skin over the open structure textile which has a pore structure with opening dimension such that the pore structure both resists tissue ingrowth and allows electrolyte penetration. Three methods for achieving this are described here.

The first method is to create the outer sheath or cover with specific textile approaches that are able to create very small pore sizes. On way to do this is to create a high-density "micro-braid" over the lead structure. The space between the individual strands defines openings, such as pores. Since the pore sizes in a braided lead can be made to approach the diameter of the filament used in the braid it is necessary to create the braid with filaments, such as multi-filament yarns, that have individual filament diameters of about 10 μm.

Alternatively, a flat tape with thickness of about 10 μm may be used. Such tapes may, for example, be made from biocompatible non-woven materials such as Dyneema®. Non-woven membrane materials made in this way can have a pore size around 1 micron, a porosity of up to 85% and a thickness of between 10 and 20 microns. It will be understood that other textile techniques, such as described in Wulfhorst, B., Gries, T., Veit. D., "Textile Technology", Carl Hanser Verlag Munich 2006, may also be used to create very fine structures with small pore sizes.

Figure 3:
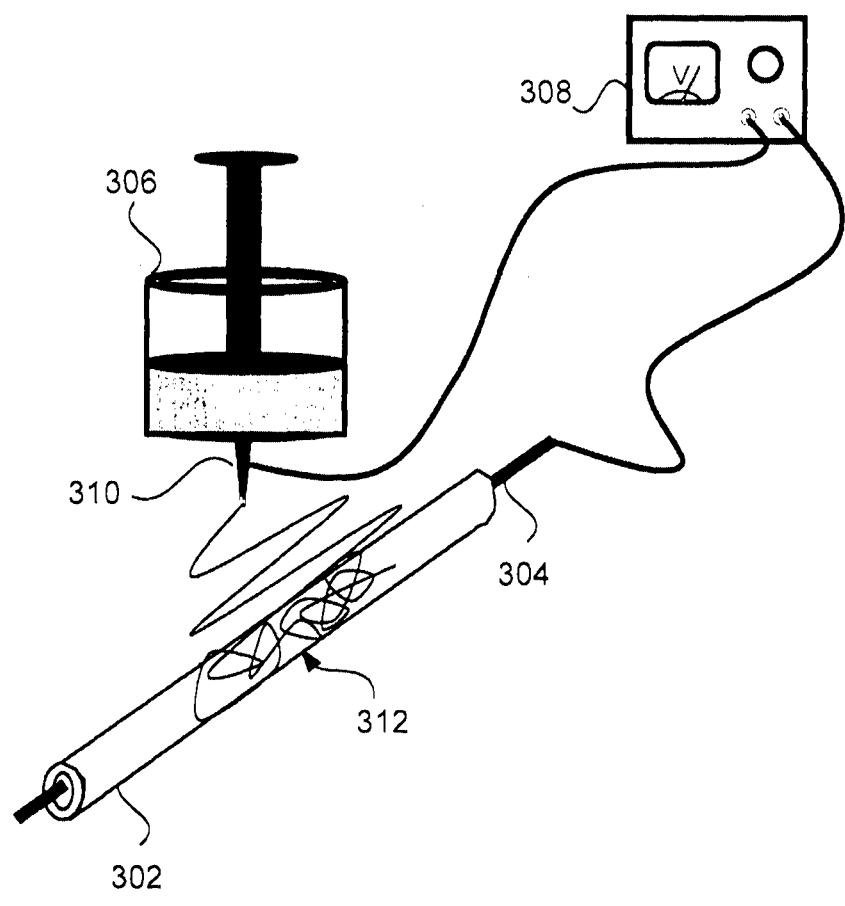
FIG. 3 illustrates the creation of a cover using an electrospinning process.

FIG. 3 illustrates how an electrospinning process may be applied to create a cover of an AIMD lead 302. The lead 302 comprises an electrically non-conductive support member and electrically conductive stimulation electrodes disposed on the support member (not shown). A conductive stylet 304 is inserted in a central lumen in the AIMD lead 302. Then, a suitable polymer material, such as PET, is loaded into a syringe deliver system 306. An high voltage source 308 is connected to the syringe nozzle 310 and the conductive stylet 304. The non-woven coating 312 is formed around the AIMD lead 302 by suitably moving the lead/stylet assembly 302/304 beneath the syringe. As a result, the lead 302, that is, the support member and the electrodes, is covered by a cover. The cover comprises openings between the strand that is formed by the electrospinning process. The movement of the lead/stylet assembly 302/304 beneath the syringe is such that the openings formed by the strand are dimensioned such that the openings allow stimulation of tissue by the electrodes while preventing tissue ingrowth.

In another example, a circular braiding machine is used. Several yarn carriers are moved in an intertwining pattern around a central former or mandrel and the yarn is woven around the mandrel. The number and type of yarns, their tension, and the braid angle are key parameters which control the density and stiffness of the resulting tube. For example, a 48 yarn braid made using with a 10 dTex Dyneema Purity® multi-filament yarn with a braiding angle of 30 degrees and yarn tension of 20 grams has been shown resist tissue ingrowth with a manageable stiffness increase.

Figure 4A:
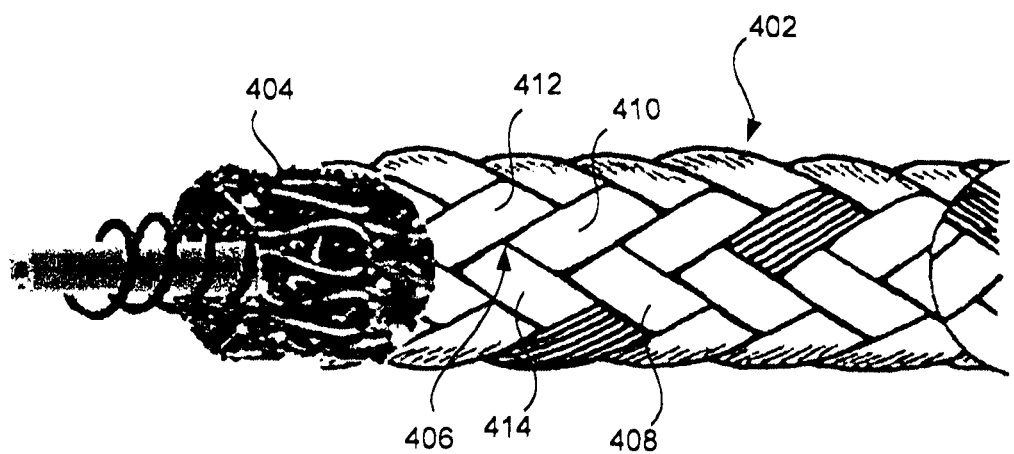
FIGS. 4a and 4b are side views of a braided cover.
Figure 4B:
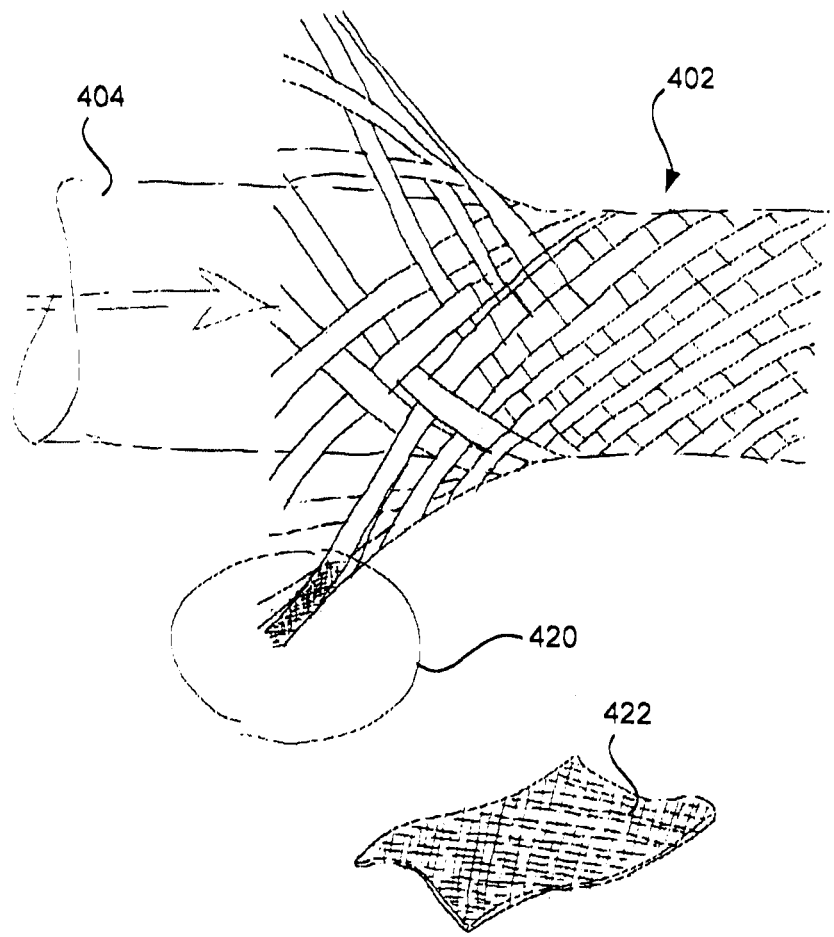

FIGS. 4a and 4b illustrate an example of a braided cover 402 on a textile lead 404. In this example, the electrodes are disposed on the textile lead 404 similar to the electrodes 214, 126 and 218 shown in FIG. 2. One opening 406, for example, is formed at the point where the four strands 408, 410, 412 and 414 contact each other. An electrode is located under this opening and as a result, the cover comprises an opening at the location where the cover covers the electrode. The cover 402 is braided such that the dimensions of the opening are such that the opening facilitates electrical conduction to allow stimulation of tissue by the electrode while preventing tissue ingrowth into the lead 404. In FIG. 4b a region 420 of the braided cover 420 is shown in a magnified representation 422.

The cover may also be a porous membrane using non-woven textiles. In the case of polymer non-wovens the fibres are arranged at random and the fabric is stabilised by applying suitable heat and pressure to ensure the fibre bond where they cross, but they do not melt. The pore size of a non-woven textile is a function of the fibre diameter and its density. Suitable biocompatible non-woven membranes may be made, for example, from ultra high molecular weight polyethylene (UHMWP) (e.g. Dyneema®). Such non-woven textiles may be cut and manipulated like all textiles and may be bonded to themselves by the application of controlled heat and pressure The second method is to wrap and fix a porous tape or membrane, such as a perforated tape, around the open textile lead structure. In this case a suitable tape is first perforated with an array of holes of suitable dimensions to both resist tissue ingrowth and allow electrolyte penetration. The tape is used to cover the textile lead. This may be achieved either by wrapping the tape helically around the textile lead so that each wind overlaps slightly with the previous one. If a smoother finish is required, a tape of width equal to or slightly larger than the circumference of the textile lead may be aligned coaxially with the textile lead and wrapped and secured in a seam where the edges of the tape overlap. In either case the tape may be secured by bonding at the overlap. Such bonding may be achieved either by use of a suitable glue or, in the case tapes made from a thermo-softening polymer, a heat bonding process (e.g. laser, hot-wheel or hot air) may be used.

Figure 5:
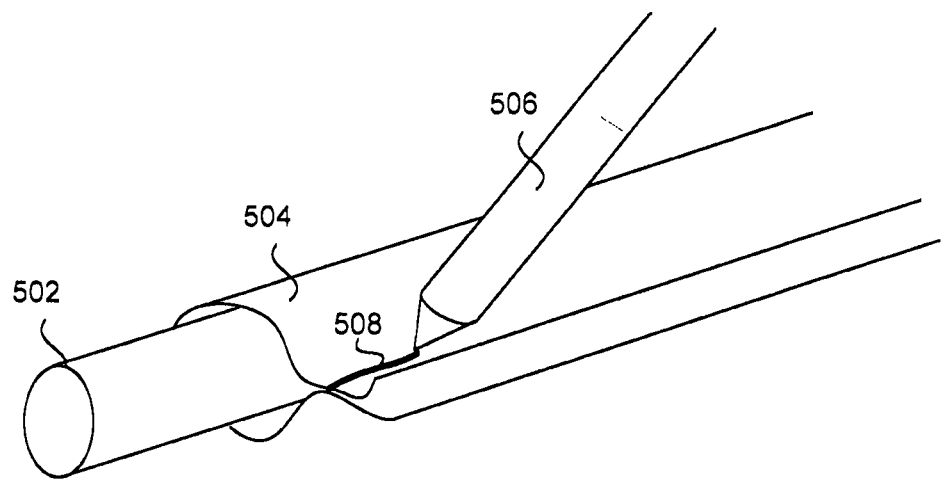
FIG. 5 illustrates the creation of a cover using a hot stylus.

FIG. 5 illustrates one exemplary method to create a membrane cover. The method comprises enfolding the AIMD lead 502 in the membrane 504, using a hot stylus 506 to bond two flaps of the membrane together along a bonding line 508 and trimming off excess membrane material.

Figure 6:
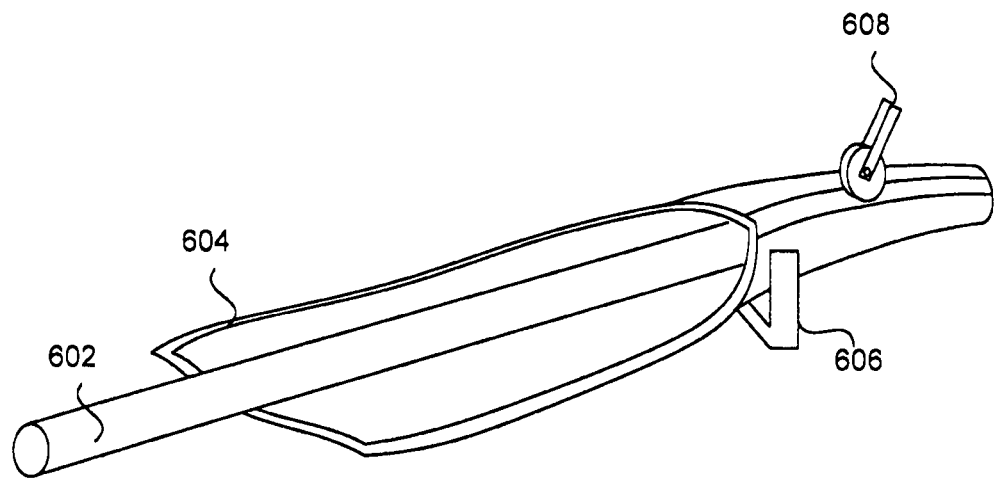
FIG. 6 illustrates the creation of a cover using a heated roller.

FIG. 6 illustrates a continuous method where the AIMD lead 602 or the part of the AIMD lead to be covered, is laid on a strip of membrane material 604. The assembly is taken to a folding jig 606, which has the effect of folding the membrane material 604 around the AIMD lead 602 with a small overlap as the assembly is moved into the jig 606. The assembly of the AIMD lead 602 and the membrane material 604 is advanced into the folding jig 606 and a heated roller 608 is used to bond the overlapping sections of the membrane material 604.

FIGS. 7a, 7b and 7c illustrate yet another method where a tight fit of the membrane is achieved. A compression assembly 700 is prepared by placing an elastomeric tube 702 (with an unexpanded inside diameter less than the diameter of the covered AIMD lead 706 in FIG. 7c) inside a solid (e.g. metal) tube 704 with an inside diameter greater than the diameter of the covered AIMD lead 706 plus twice the wall thickness of the elastomeric tube 702.

The end of the elastomeric tube 702 is then expanded and folded back over the outside of the solid tube 704 as indicated by two arrows. A length of elastomeric tube 702 at least as long as the covered potion of the AIMD lead 706 must be folded back. The part of the AIMD lead 706 to be covered is laid on a strip of membrane material 708.

The assembly of the lead 706 and the membrane 708 is passed through a folding jig 606 which has the effect of folding the membrane material 708 around the AIMD lead 706 with a small overlap as the assembly is moved into the jig 606. The AIMD lead/membrane assembly 706/708 is advanced through the folding jig 606 and into the compression assembly 700. As the lead/membrane assembly 706/708 is advanced into the compressions assembly 700 the elastomeric tube 702 is pulled into the solid tube 704, contracting around the membrane material 708 folded around the AIMD lead 706 and a uniform force is applied onto the membrane material 708 at all points. The encapsulated lead/membrane assembly 706/708 may then be placed in an oven and heated in a controlled environment to ensure a good bond between the overlapping parts of the membrane 708. At the completion of this operation the elastomeric tube is removed and may be reused the next time the procedure is conducted.

The third method to create a skin or cover over an open textile structure is to use a porous polymer tube of suitable biocompatible material and dimensions and which has property that it can be made to shrink, for example with the application of heat or a chemical agent. An example of such a material is PET. This material contains many monomers which polymerise when it is heated. This increases the density of the material and the material shrinks. A wide range of thin wall heat-shrink tubing is available. Such materials may be selected for their strength, shinkage ratios and the stiffness they impart to the covered electrode. The properties of such material are selected such that a tube that is initially slightly larger than the unprotected textile lead will shrink to become a tight fit over the textile lead without excessive change in the tube wall thickness or increase in the tube wall thickness. Such a tube is first made porous by perforating the tube with an array of holes of suitable dimensions to both resist tissue ingrowth and allow electrolyte penetration. The tube is then slid over the open textile lead and shrunk (for example by the application of heat) to form a tight fit over the open textile lead. In this case care must be taken in material selection to ensure that the lead does not become too stiff once the heat shrink tube is shrunk.

FIG. 8 illustrates an active implantable medical stimulation device 800. The device 800 comprises an electrically non-conductive support member 802, two electrically conductive stimulation electrodes 804 and 806 and a cover 808. In this example, the cover surrounds the support member 802 and is therefore shown as two parts 808 and 808' in the cross-section.

The stimulation electrodes 804 and 806 are disposed on the support member, which may be achieved in a variety of ways. In one example, the electrodes are disposed on a knitted support member by wrapping a conductive filament around non-conductive filaments of the support member as shown in FIG. 2. In other examples, the electrodes 804 and 806 are disposed on the support member by attaching the electrodes 804 and 806 to the outside of the support member, by moulding the electrodes 804 and 806 into the support member 802 or by other means. It is to be understood that the electrodes 804 and 806 which are disposed on the support member may be partly within the support member, may protrude from the surface of the support member 802 or may be flush with the surface of the support member 802. In another example, the electrodes 804 and 806 are metal sheets which are disposed on the support member 802 by being located on the outside of the support member and held into place by fasteners or the cover 808.

The cover 808 covers the support member 802 to prevent ingrowth into the support member 802. In examples where tissue needs to be prevented from ingrowing into only parts of the support member 802, the cover 808 needs to cover only those parts and not the entire support member 802.

The cover 808 also covers the electrodes 804 and 806. At locations 814 and 816 where the cover 802 covers the electrodes 804 and 806, respectively, the cover comprises one or more openings, such as pores. The openings at the locations 814 and 816 are large enough to allow stimulation and small enough to prevent tissue ingrowth, that is, the openings are dimensioned such that the openings facilitate electrical conduction and therefore allow stimulation of tissue by the electrodes while preventing tissue ingrowth. Examples of the dimension of the openings is given earlier. In another example, the cover comprises openings on the entire surface of the cover and not only at locations 814 and 816.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An active implantable medical stimulation device, the device comprising:
   an electrically non-conductive support member having an open textile structure;
   one or more electrically conductive stimulation electrodes disposed on the support member; and
   a cover covering the support member and the one or more electrodes, wherein at locations where the cover covers the electrodes, the cover comprises one or more openings dimensioned such that the one or more openings allow stimulation of tissue by the electrodes while preventing tissue ingrowth, the cover being a porous flexible material that fills the open textile structure.

2. The device of claim 1, wherein the porous flexible material is biocompatible.

3. The device of claim 1, wherein the porous flexible material has openings at least where the cover covers the one or more electrodes.

4. The device of claim 1, wherein the one or more electrodes are formed by a textile technique.

5. A method for creating an active implantable medical stimulation device, the device comprising an electrically non-conductive support member having an open textile structure and one or more electrically conductive stimulation electrodes disposed on the support member, the method comprising:
   forming a cover for covering the support member and the one or more electrodes by filling the open textile structure with a flexible material that prevents tissue ingrowth such that at locations where the cover covers the electrodes, the cover comprises one or more openings dimensioned such that the one or more openings allow stimulation of tissue by the electrodes while preventing tissue ingrowth.

6. The method of claim 5, wherein the material that prevents tissue ingrowth is biocompatible.

7. The method of claim 6, wherein forming the cover further comprises:
   coating the one or more electrodes with a sacrificial coating before filling the open textile structure; and
   removing the sacrificial coating after the filling has cured;
   wherein the thickness and size of the sacrificial coating is such that one or more openings are formed in the cover, the openings being dimensioned such that the one or more openings allow stimulation of tissue by the electrodes while preventing tissue ingrowth.

8. The method of claim 5, wherein forming the cover further comprises:
   prior to filling the open textile structure with the flexible material that prevents tissue ingrowth, adding finely ground biocompatible material that is soluble in a biocompatible fluid to the flexible material that prevents tissue ingrowth; and
   after the flexible material that prevents tissue ingrowth has been cured, dissolving the finely ground biocompatible material in the biocompatible fluid, thereby providing openings that provide a conduction path for ions in the material that prevents tissue growth.

9. The method of claim 5, further comprising laser drilling suitable size openings through the flexible material over the one or more electrodes.

* * * * *